United States Patent [19]
Ricci et al.

[11] Patent Number: 4,774,056
[45] Date of Patent: Sep. 27, 1988

[54] APPARATUS FOR TESTING SEDIMENTATION RATES OF LIQUIDS

[75] Inventors: Antonio Ricci, Siena; Luciano Romoli, Florence, both of Italy

[73] Assignee: Diesse Diagnostica Senese S.r.l., Italy

[21] Appl. No.: 862,127

[22] Filed: May 12, 1986

Related U.S. Application Data

[63] Continuation of Ser. No. 521,417, Aug. 8, 1984, abandoned.

[51] Int. Cl.$^4$ .......................................... G01N 31/16
[52] U.S. Cl. ........................................ 422/73; 422/63; 436/70; 435/291; 356/39; 73/64.1
[58] Field of Search ............... 422/63, 73, 102, 99, 422/104; 435/291–294, 808, 809; 436/50, 70; 346/33 ME; 73/64.1; 356/39; 366/239, 240

[56] References Cited

U.S. PATENT DOCUMENTS

| | | | |
|---|---|---|---|
| 3,715,761 | 2/1973 | Richter et al. | 356/39 |
| 3,718,439 | 2/1973 | Rosse et al. | 422/102 |
| 4,265,544 | 5/1981 | Banno et al. | 422/68 |
| 4,278,437 | 7/1981 | Haggar | 422/73 |
| 4,336,880 | 6/1982 | Mehl | 422/102 |
| 4,457,894 | 7/1984 | Clark et al. | 422/68 |

Primary Examiner—Barry S. Richman
Assistant Examiner—Timothy M. McMahon
Attorney, Agent, or Firm—McGlew and Tuttle

[57] ABSTRACT

The apparatus consists of at least one test-tube carrier defining seats for test tubes. The carrier is moved by oscillation or rotary motion about a horizontal axis under the influence of time control means. A structure which is vertically movable relative to the test tubes is fitted with individual means for the photometric observation of the data relating to each test tube and is controlled by time-control means. Processing and recording means collect data relating to the presence of each test tube, the presence of a sample, and the level of said sample, for each test tube seat.

8 Claims, 3 Drawing Sheets

APPARATUS FOR TESTING SEDIMENTATION RATES OF LIQUIDS

This is a continuation of application Ser. No. 521,417 filed Aug. 8, 1984, now abandoned.

BACKGROUND OF THE INVENTION

1. Technical Field

The present invention relates to apparatus for determining the blood erythrosedimentation (ESR) of a plurality of blood samples, and for similar sedimentation tests on other liquids.

2. Prior Art

It has long been known that the erythrocytes present in the blood of subjects suffering from various diseases sediment more quickly. The increase of the blood erythrosedimentation rate (ESR) is due essentially to alterations of the plasmatic and erythrocytic factors intervening, which promote the formation of rouleaux.

The traditional method of measurement of the blood ESR is Westergren's. 4 ml of venous blood is mixed with 1 ml of anti-coagulant (a 3.1% solution of sodium citrate). A pipette (for example a glass pipette, 30 cm long and gauged in millimeters from 0 to 200) is filled by suction exactly to the mark 0, and then it is mounted on a suitable pipette holder in a perfectly vertical position. It is left at ambient temperature for 60 minutes, after which the result is read off (1st hour). The distance in millimetres between the plasmatic meniscus and the erythrocyte one represents the value of the erythrocyte sedimentation rate (ESR). The reading may be repeated after a further 60 minutes (2nd hour).

Another method is that described by Wintrobe in which use is made of a hematocrit tube. In this method also the results are expressed in millimetres per hour. A number of variations have been introduced into these methods; among the most important of these mention may be made of micro-methods and sedimentation in a pipette inclined at 45° to accelerate ESR and reduce reading times.

All the methods mentioned above exhibit a number of drawbacks. These methods, though they can be simply followed commit for a not unappreciable time the laboratory technician who has to carry out a fairly substantial number of examinations. In addition, in the course of handling, as the pipettes are filled by suction with the mouth, there occur for the operator serious possibilities of coming into direct contact with samples of infected blood.

In addition there are the following possibilities of errors:

(1) if the exact concentration of anti-coagulant in the blood is greater than anticipated, this reduces the ESR;

(2) If the pipette is not clean and contains traces of detergents, alcohol, ether or other compounds this affects the results;

(3) If the pipette is not completely vertical this introduces errors, for example an inclination of only 30° from the vertical may accelerate ESR by 30%;

(4) If the temperature is not around 20° C. or not higher than 27° C. this may affect the results and, in addition, the exposure of pipettes to the sun's rays affects the results;

(5) If the reading is not made at the correct time the result will be affected;

(6) If the supporting plane is subject to vibration or movement this alters readings;

(7) Errors also occur both during the pipette filling stage (using one sample for another, imprecise resetting) and during reading off and manually transcribing the data.

SUMMARY OF THE INVENTION

The object of the present invention is to provide an appliance able to automatize the operations for the determination of ESR in the blood and other similar blood tests.

The present invention provides apparatus for testing a plurality of samples of liquid simultaneously, including at least one test-tube-carrier defining a plurality of seats for test tubes, means for moving said carriers in oscillation about a horizontal axis, means for the time control of said movement and for stopping the arrangement with the test tubes in vertical positions, a structure provided with individual means for the photometric observation of data relating to each test tube, means for moving said structure vertically relative to the test tubes, means for the time interval control of the relative displacements between said structure and the test tubes, and means for processing and recording data collected by each said observation means, said data including observations of the presence of the test tube, presence of the sample, and of the level of said sample, for each seat and for each observation means.

DESCRIPTION OF PREFERRED EMBODIMENTS

Figures 1, 2, 3, 4, 5:
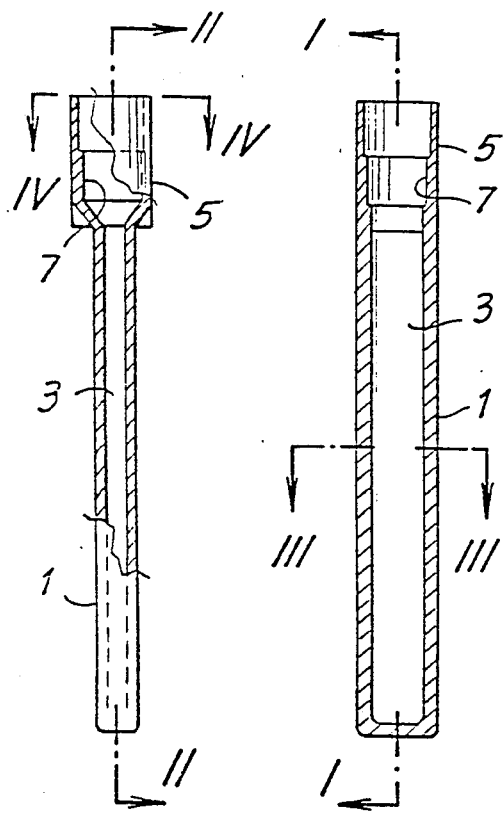
FIGS. 1, 2, 3 and 4 show cross-sections respectively along the lines I—I of FIG. 2, II—II of FIG. 1, III—III of FIG. 2, and IV—IV of FIG. 1, of a test tube for use in the testing apparatus.
FIG. 5 shows a detail of FIG. 1 with a plug applied.

Test tubes for containing samples of blood or other liquid for which the sedimentation rate is to be estimated for use in the testing apparatus are illustrated in FIGS. 1 to 5 of the accompanying drawings. The test tube has an elongated body 1, with a rectangular cross-section with a hollow cavity 3. Body 1 has two narrow sides and two sides. At the opposite end to the bottom of the test tube there is provided a head 5 of circular section, the outer diameter of which corresponds approximately to the greater outer dimension of the rectangular section of the body of the test tube (FIG. 4). In the head, a seat 7 is formed, able to house a closure seal or cap for the test tube generically denoted by 9 (FIG.5). The closure seal is inserted by forcing. The test tube may be mostly made of relatively rigid synthetic resin and the closure seal 9 of relatively more yielding material. The test tubes may be of throw-away or reusable type.

Seal or cap 9 has a head portion on the top which has a diameter larger than the inside diameter of the head 5 so that the head portion of cap 9 sits on the upper rim of head 5. Cap 9 also has a plurality of rings on its outer surface below its head portion adjacent the seat 7. Head 5 of the test tube is connected to body 1 by inclined wall portions as shown in FIG. 5. A plurality of ribs extend outwardly from the inclined wall portions and form a part of head 5, as also seen in FIG. 5.

A sample of liquid to be examined is introduced into each test tube. In the particular case of the examination of blood erythrosedimentation (ESR) there may be present in the test tube a suitable anti-coagulant such as tribasic sodium citrate in a suitable aqueous solution. The anti-coagulant may be pre-packaged in the test tube in an amount already predetermined for examination.

Figure 6:
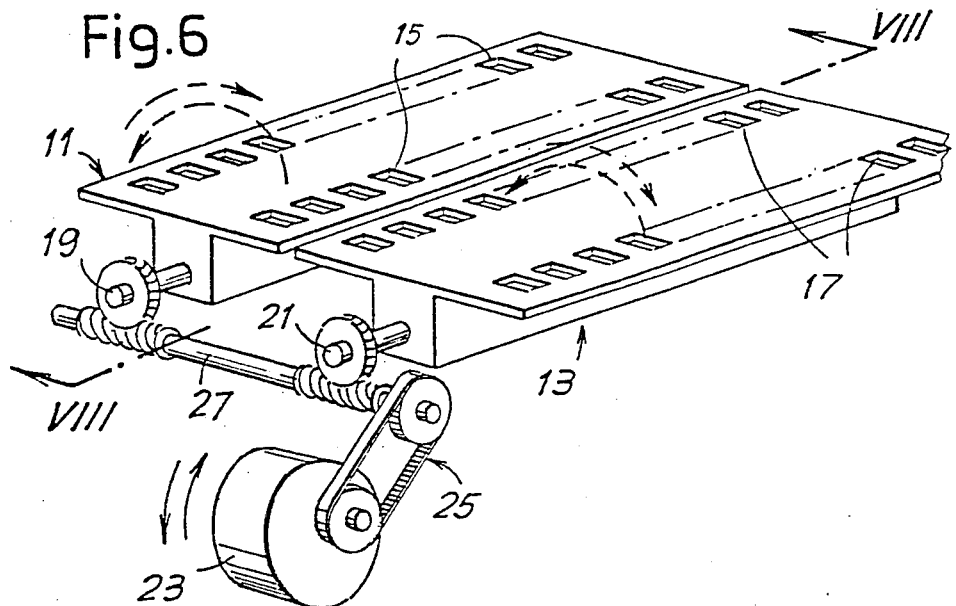
FIGS. 6 and 7 show in perspective and diagrammatically elements of the apparatus.
Figure 8:
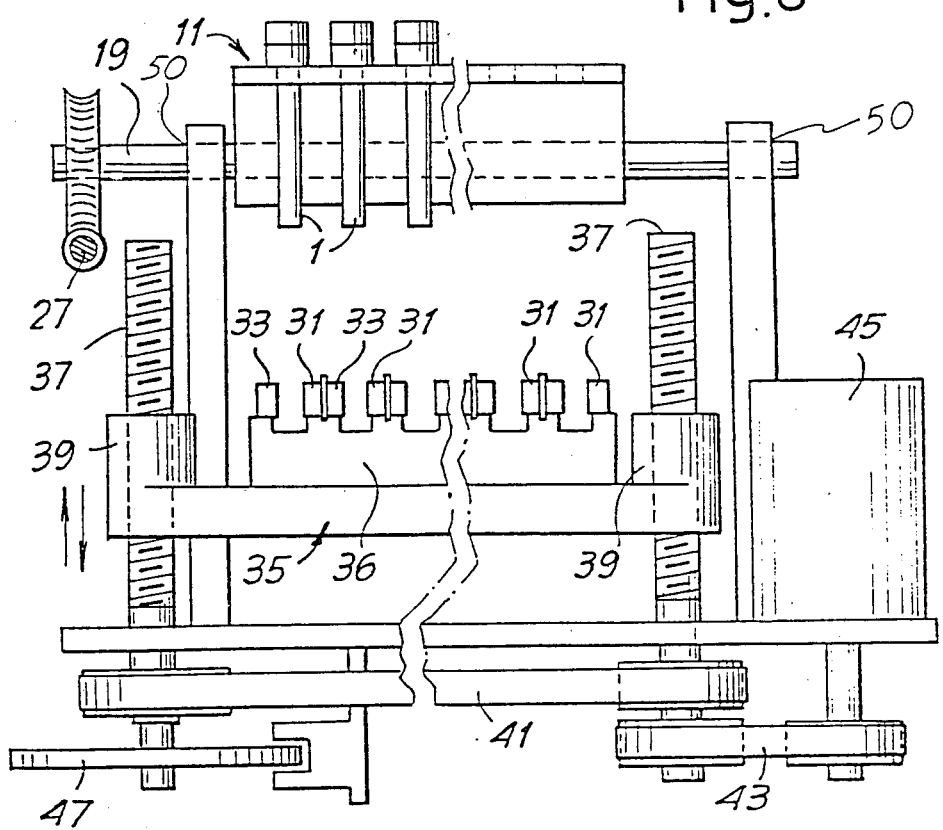
FIG. 8 shows a diagrammatic cross-section substantially along VIII—VIII of FIG. 6.
Figure 7:
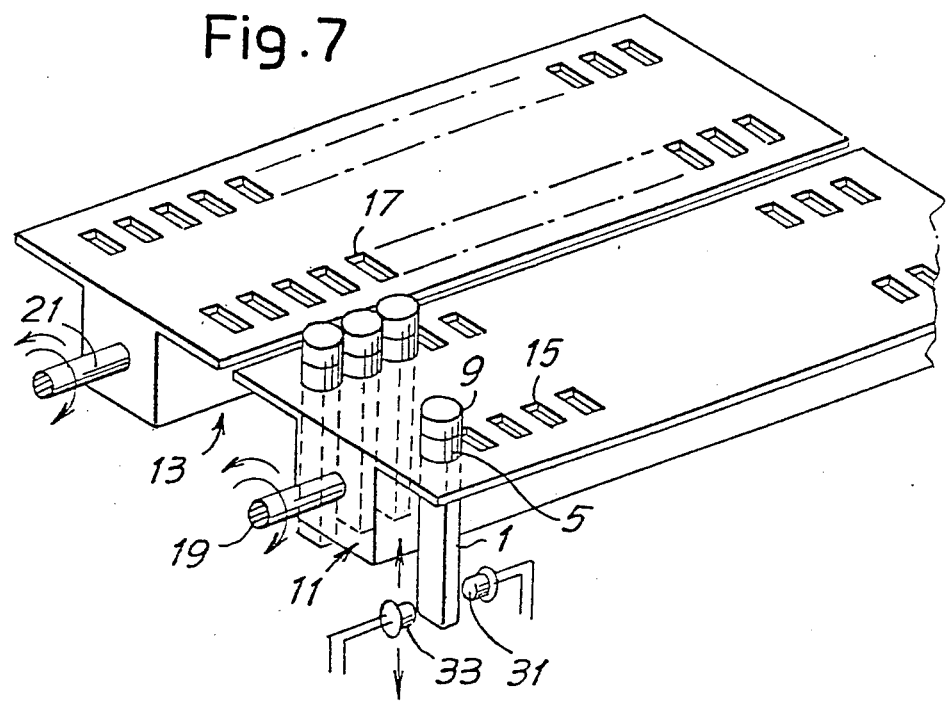

The apparatus comprises, in the embodiment illustrated, two carriers 11 and 13 which each have a plate portion with a plurality of test tube seats 15 and 17 able to house the test tubes holding them by means of their heads 5 so that their bodies 1 protrude below the respective seats 15 and 17 of the two carriers 11 and 13. In the embodiment represented, the two carriers 11 and 13 each have a plane including two flanged projections in each of which a row of seats 15,17 respectively is defined for the test tubes. Each seat 15 or 17 comprises a rectangular opening. The head 5 of each test tube rests on the respective carrier around one of the seats. Each of these four rows has fifteen seats for test tubes. Thus the apparatus enables sixty samples to be examined at the same time. The two carriers 11 and 13 are mounted on end pivots or oscillation shafts 19 and 21, in such a way as to permit oscillation of the two carriers about respective parallel horizontal axes along a vertical plane of symmetry passing through the oscillation shafts 19, 21 to obtain the stirring action of the samples. Shafts 19 and 21 are supported on mounting means or bearings 50 for this purpose. To effect automated shaking, it is possible to provide joint means for the choking oscillation of the two carriers. The shaking is in a direction parallel to the wide sides of the test tube 1 (FIG. 6). The rest position of the carriers is such that the test tubes are vertical. In FIGS. 6 and 8 there is shown a mechanical moving means for carrying out the shaking operation and oscillation which consists of a motor 23, a belt transmission 25 and a shaft 27 with two worm screws to control in symmetrical manner the movement of the two carriers with worm and helical wheel couplings, the latter mounted on the pivots or oscillation shafts. Each pivot or shaft 19, 21 extends over the casing 11, 13 near the middle of the test tube bodies and into the body portion of each carrier 11, 13, the body portion extending below the plate portion thereof 11, 13. Shafts 19, 21 also extend parallel to the rows of seats 15, 17 and between the two rows for each carrier.

The apparatus also comprises means for making photometric observations or readings along the body 1 of each test tube. For this purpose provision is made for photometric reading systems with photo-electric cells and illuminator lamps such as denoted by 31 and 33. A set of photo-electric cells and respective lamps associated therewith are provided for carrying out readings on the test tubes in each row of seats 15 and 17. A single structure may be provided for moving all the photometric sets vertically relative to the bodies of the test tubes arranged in the rows of seats for test tubes of both carriers 11 and 13. A sensor support member or structure 35 may be provided for raising and lowering the observation means relative to the arrangements 11 and 13 in the direction of the bodies 1 of the test tubes inserted in the test tube carriers. The structure 35 has—in the form of combs 36 or the like—rows of photo-electric cell sensors and rows of corresponding lights. The structure 35 is moved by means of threaded columns 37 engaging nuts 39 for translation. These nuts 39 engage the structure 35, these connections may yield as appropriate. The two or more threaded columns 37 may be simultaneously controlled by a toothed belt transmission 41 and a transmission means 43 actuated by a motor 45 which may be a stepping motor or other type of motor. To the kinematic system of the columns 37 it is possible to connect a suitable metering device 47 including a notched disc and relevant reading device, for measuring the angular displacements of the columns and therefore the linear vertical displacement of the structure 35 and of the photo-electric systems 31 and 33 along the bodies 1 of the test tubes.

Figure 9:
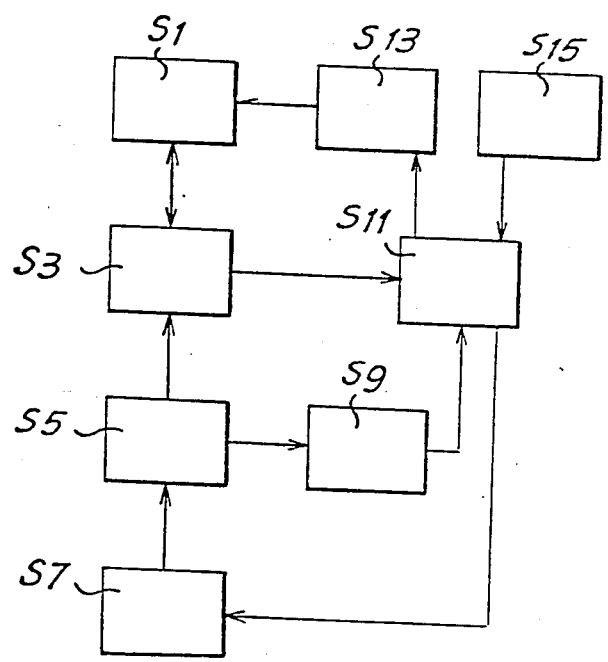
FIG. 9 shows a block diagram to illustrate the functions and functional connections of the parts of the apparatus.

The diagram of FIG. 9 shows symbolically the test tube carriers S1, the photometric readers observation means S3 the structure moving means S5 corresponding to the threaded columns 37, the displacement motor 45, S7, the device S9 for measuring the height of the photometric readers to stop the same, an electronic processor S11, the motor S13 of the shaker, i.e. motor 23 and a control panel S15. The lines and arrows indicate the functional connections between the various items.

For the ESR measurements, there are sent from the photometric readers to the processor three data for each sample examined. Readings are effected at times: 0 minute (corresponding to the moment when after shaking the blood has stopped flowing and its level is stabilized), 30 min. and 60 min. These data called X1 and X2 and X3 are processed as follows:

$$Z1 = ((X1 - X2)/X1) \cdot 100$$

$$Z2 = ((X1 - X3)/X1) \cdot 100$$

$$\text{ESR 1st hour} = f(Z1)$$

$$\text{ESR 2nd hour} = f(Z2)$$

$$\text{Katz index} = f(Z2)/2 + f(Z1)/2$$

The function employed in the calculations is the equivalent of a straight line function. By means of a switch it is possible to programme the instrument in such a manner that readings occur only at 0 and 30 min. times; in this case there is obtained only the value of ESR 1st hour and the Katz index is not calculated.

A suitable printer provides for the printing of the data acquired and the results of the processing by the electronic processor.

The apparatus is equipped with a control panel comprising: an ON-OFF switch for the instrument; two selector switches which permit reading at the first hour, at the second hour or at both; a switch which actuates the operating cycle of the instrument.

The automatic method for the determination of the ESR of blood with the described apparatus is carried out as follows. Each test tube is filled with blood by means of a syringe, up to the reference mark; it is plugged, the contents are shaken so as to avoid the coagulation of the blood, and it is placed in a test tube seat in a carrier 11 or 13. By means of the change-over switch a selection is made of the type of results desired (ESR 1st hour and ESR 2nd hour) and the switch is pressed which actuates the operating cycle of the instrument.

The stages of shaking, reading, data processing and presentation of the results are performed automatically by the instrument—suitably programmed—in the manner indicated below.

The agitator effects the oscillation of the test tubes disposed in their seats on the test tube carrier, with oscillations relative to the vertical rest position. This produces a substantially perfect mixing of the corpuscular part of the blood with its plasma and any rouleaux formed are broken up.

A few minutes after the end of shaking the optical reader is activated. The latter is programmed in such a manner that until the light emitted by the last transmitter strikes the corresponding sensor the reader is raised vertically, thus measuring the height of the blood column, which is optically opaque. The reading relevant to each test tube is memorized by the processor and is denoted by X1. Previous to this operation, the reader reveals the presence of the test tube and also of an amount of blood sufficient for analysis, effecting a measurement at 5 mm from the bottom of the test tube, to check the first event, and a measurement at 55 mm to check the ground.

At the level of, e.g. 65 mm there is present a photocell which prevents the photometric reader from exceeding this level. When this limit level is reached the motor reverses the direction of oscillation until the photometric unit is returned to zero level. When this condition occurs this is also indicated at the final results printing stage.

The time measuring device is then activated for 30 minutes. During this time the corpuscular part of the blood sediments, leaving the liquid plasma at the top, this, as opposed to the corpusculate part, is optically transparent. At the end of 30 minutes the reader is again activated; it measures for each test tube the height of the sedimented erythrocytes. The reading is memorized and denoted by X2.

If the switch which eliminates reading at 60 minutes has been set, the cycle is finished and the processed data are despatched to the printer; otherwise the time measurement and reading functions are repeated in order to have the third reading denoted by X3, with which it is possible to calculate the ESR at the second hour and the Katz index. The processing of the data being completed for all test tubes present, the printing phase follows.

The values which are presented by the instrument may be expressed in mm per hour and are comparable with those which would have been found if the reaction had been conducted according to Westergren's method. The function which connects the two methods was found experimentally by analyzing 25 blood samples by both methods. From the data obtained experimentally it follows that the two methods are corrected to a high degree, that the points found are highly significant for the equation of a straight line and that said straight line has the following equation $y = 1.763 + 0.595x$ where x is the abscissa and y is the ordinate with the values of Westgreen's method being plotted on the x axis and the values according to the present invention plotted on the y axis.

It will be understood that the drawings show only one example given of a practical realisation of the apparatus. Various modifications may be made, for example, the presentation of the final results may be effected—as alternatives—on alpha-numerical and/or numerical displays constructed in accordance with various technologies (LED, lCD, gas, magnetic), with video terminals, transmitted from an interface for subsequent processing. The system may be extended to provide for a larger number of test tubes, or reduced for a smaller number of test tubes. The test tubes may be made with transparent materials which may be other than plastic, or the geometry of the test tubes may be different from that illustrated, for example, each test tube may have a circular, polygonal, elliptic or other section.

We claim:

1. An apparatus for testing a plurality of samples of liquid simultaneously, comprising:

a plurality of test tubes, each test tube having an elongated body with a central longitudinal axis and a rectangular cross-section orthogonal to the central longitudinal axis of the tube, each test tube having a pair of narrow sides and a pair of wide sides, a head which is circular in horizontal cross-section orthogonal to the central longitudinal axis of the tube which is fixed to said elongated body, said test tube having a diameter which is about equal to a width of each wide side of said elongated body;

a test tube carrier having a plate portion with means defining a plurality of through openings therein lying in at least one row extending in a first horizontal direction, each opening being of a size to receive said elongated body of one of said test tubes and to preclude entry of said head of one of said test tubes, said test tube carrier having a body portion connected to said plate portion and spaced from said at least one row of through openings in said plate portion;

each of said plurality of test tubes having its elongated body inserted into one of said through openings with said head of each test tube being supported on an upper surface of said plate portion around each respective through opening with said wide sides of each elongated body extending in a second horizontal direction which is perpendicular to said first horizontal direction;

an oscillation shaft connected to said body portion of said carrier and extending parallel to said first horizontal direction;

mounting means for supporting said oscillation shaft;

drive means operatively connected to said oscillation shaft for oscillating said carrier about said oscillation shaft and in a direction parallel to said wide sides of said test tubes;

control means for activating said drive means for stopping said drive means with said test tubes in a vertical position;

a sensor support member carrying a plurality of sensor means lying in a row parallel to said at least one row of through openings, each sensor means being in a position for facing a wide side of a test tube in one of said through openings, said sensor support member carrying a number of sensor means equal to said number of through openings in said test tube carrier;

vertical movement means operatively connected to said sensor support member for moving said sensor support member vertically to move said sensor means toward said through openings and past said wide sides of said test tubes;

timing means for activating said vertical movement means during selected time intervals; and data processing means connected to said sensing means for processing and recording data collected from said sensing means including data concerning the presence of a test tube in each through opening, the presence of a liquid sample in each test tube and the level of the sample in each tube.

2. An apparatus according to claim 1, wherein each test tube includes an inclined wall portion connected between said head and said elongated body, said head having means defining an inner opening defining a seat with a circular cross section, and a resilient cap engaged in said seat, said head of said test tube having an upper rim, said cap having a head engaged against said upper rim.

3. An apparatus according to claim 1, wherein said body portion of said carrier extends downwardly from said plate portion portion of said carrier, said plate portion extending to opposite sides of said body portion in said second horizontal direciton, said plate portion carrying two rows of through openings with said two rows being positioned and arranged on said plate on opposite sides of said body portion, each row extending parallel to said first horizontal direction, said oscillation shaft connected to and extending from said body portion at a location below said through openings in said plate portion and between said two rows of through openings, said carrier having a vertical plane of symmetry passing through the axis of said oscillation shaft.

4. An apparatus according to claim 3, wherein said sensor support member carries a comb shaped structure having teeth, said sensor means being mounted on said teeth, each sensor means comprising a photoelectric coil on one tooth of said comb and a light emitter on an immediately adjacent tooth of said comb, said teeth being spaced apart for recevieing the elongated body of a test tube therebetween when said sensor support member is moved vertically toward said carrier.

5. An apparatus according to claim 4, wherein said drive means comprises a worm shaft, having a worm thereon, mounted for rotation of said worm shaft parallel to said second horizontal direction, a worm gear fixed to said oscillation shaft and meshed with said worm and a motor operatively connected to said worm shaft for rotating said worm shaft.

6. An apparatus according to claim 4, wherein said vertical movement means comprise a pair of spaced apart rotatably mounted threaded columns, a pair of nuts fixed to said sensor support member and threadably receiving each of said threaded columns respectively, motor means operatively connected to said columns for rotating said columns in one direction for raising said support member and in an opposite direction for lowering said support member, said data processing means including a disc fixed to one of said columns rotatable with rotation of said column and a reading device mounted adjacent said disc for reading markings on said disc to provide a reading corresponding to a vertical position of said support member.

7. An apparatus according to claim 6, wherein said nuts are positioned on opposite sides of said comb, said threaded columns being rotatably mounted on opposite sides of said comb, said threaded columns extending vertically, said drive means comprising a worm shaft having a worm extending in said second horizontal direction, a motor operatively connected to said worm shaft for rotating said worm shaft and a worm gear fixed to said oscillation shaft and meshed with said worm.

8. An apparatus according to claim 7, wherein each test tube includes an inclined wall portion connected between said head and said elongated body, said head having means defining an inner opening defining a seat with a circular cross section, and a resilient cap engaged in said seat, said head of said test tube having an upper rim, said cap having a head engaged against said upper rim.

* * * * *